United States Patent [19]
Rule, Jr.

[11] Patent Number: 6,129,817
[45] Date of Patent: *Oct. 10, 2000

[54] UNIFIED ON-LINE/OFF-LINE PAPER WEB FORMATION ANALYZER

[75] Inventor: James Arthur Rule, Jr., Covington, Va.

[73] Assignee: Westvaco Corporation, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/891,139

[22] Filed: Jul. 10, 1997

[51] Int. Cl.⁷ .............................. D21F 7/06; G01N 21/86
[52] U.S. Cl. .................. 162/253; 162/254; 162/263; 250/559.06; 250/559.08; 356/237.1
[58] Field of Search ................ 162/253, 25, 198, 162/DIG. 11, 263; 356/249, 237.1; 250/559.01, 559.06, 559.08; 73/159

[56] References Cited

U.S. PATENT DOCUMENTS

| | | |
|---|---|---|
| 3,661,701 | 5/1972 | Al-Shaikh ........................... 162/198 |
| 3,936,665 | 2/1976 | Donoghue . |
| 4,574,624 | 3/1986 | Lehtinen et al. . |
| 4,584,058 | 4/1986 | Lehtinen et al. ........................ 162/205 |
| 4,644,174 | 2/1987 | Ouellette et al. . |
| 4,648,712 | 3/1987 | Brenholdt . |
| 4,680,089 | 7/1987 | Aral et al. . |
| 4,707,223 | 11/1987 | Sabater et al. . |
| 4,899,061 | 2/1990 | Hoek et al. ........................... 356/560 |
| 4,936,141 | 6/1990 | Anderson, Jr. et al. . |
| 4,955,720 | 9/1990 | Blecha et al. . |
| 5,011,573 | 4/1991 | Niemi . |
| 5,013,403 | 5/1991 | Chase . |
| 5,104,488 | 4/1992 | Chase . |
| 5,316,622 | 5/1994 | Babinsky et al. ...................... 162/205 |
| 5,340,442 | 8/1994 | Gess et al. . |
| 5,461,030 | 10/1995 | Lindenbaum . |
| 5,472,571 | 12/1995 | Niemi . |
| 5,492,601 | 2/1996 | Ostermayer et al. . |
| 5,571,380 | 11/1996 | Fallon . |
| 5,584,966 | 12/1996 | Moffett . |
| 5,899,595 | 5/1999 | Shields et al. ........................ 356/237 |
| 5,899,959 | 5/1999 | Shields et al. ........................ 702/35 |

*Primary Examiner*—Steven Alvo
*Attorney, Agent, or Firm*—J. R. McDaniel; R. L. Schmalz

[57] ABSTRACT

Paper web formation analyzers can be employed both on operating paper machines at high speed and on cut samples as a desk top unit, so as to unify formation evaluation for both situations.

1 Claim, 3 Drawing Sheets

UNIFIED ON-LINE/OFF-LINE PAPER WEB FORMATION ANALYZER

BACKGROUND OF THE INVENTION

1. Field of the Invention

This invention relates to paper web formation analyzers. Such structures of this type, generally, can be employed both on paper machines operating at high speed and on cut samples as a desk top unit, so as to unify formation evaluation for both situations.

2. Description of the Related Art

It is well known, in the paper making industry, to make use of various sheet material characteristic measuring devices. Exemplary of such prior art is U.S. Pat. No. 3,936,665 ('665) to J. F. Donoghue, entitled "Sheet Material Characteristics Measuring, Monitoring and Controlling Method and Apparatus Using Data Profile Generated and Evaluated by Computer Means". While the '665 patent teaches the control of primary paper properties such as basis weight, moisture and caliper, the focus of the '665 patent is more for control of primary properties than in evaluating sheet formation. Consequently, a more advantageous analyzer, then would be presented if sheet formation could also be evaluated.

It is also known, to employ a single point measuring technique to measure sheet formation as well as other primary paper properties, such as, paper strength. Exemplary of such prior art is U.S. Pat. No. 5,104,488 ('488) to L. M. Chase, entitled "System and Process for Continuous Determination and Control of Paper Strength", U.S. Pat. No. 4,707,223 ('223) to J. Sabater et al., entitled "Apparatus for Measuring the State of Formation of a Sheet of Paper", U.S. Pat. No. 4,648,712 ('712) to I. F. Brenholdt, entitled "Apparatus and Method for Analyzing Parameters of a Fibrous Substrate", and U.S. Pat. No. 4,644,174 ('174) to R. J. Ouellette et al., entitled "Apparatus for Analyzing the Formation of a Paper Web". While the '488, '223, '712, and '174 patents teach the use of an apparatus to measure sheet formation, these employ a single point sensor to infer overall sheet formation. This single point sensor, typically, is either fixed or scanning, but at any point in time, only a single area is being studied. Consequently, a still further advantageous analyzer, then would be presented if a wider inspection area can be studied, while giving a quantitative picture of what is going on with respect to a paper formation.

It is apparent from the above that there exists a need in the art for a paper web formation analyzer which can provide a wide inspection area while giving a better quantitative picture of paper formation, but which at the same time is capable of being used both on operating paper machines and on cut samples. It is a purpose of this invention to fulfill this and other needs in the art in a manner more apparent to the skilled artisan once given the following disclosure.

SUMMARY OF THE INVENTION

Generally speaking, this invention fulfills these needs by providing an online/offline paper web formation analyzer, comprising a paper web having first and second sides, a paper web translating means, a plurality of paper web illumination means substantially located adjacent to the first side of the paper web, a plurality of paper web formation detection means located substantially adjacent to the second side of the paper web and across from the illumination means, and a paper web translating rate measurement and illumination/detection synchronization means operatively connected to the paper web translating means, the illumination means and the detection means.

In certain preferred embodiments, the paper web translating means is a pinch roller drive having a nip. Also, the paper web translating rate measurement means is a tachometer. The illumination means are preferably fiber optic, reflected-light sources. Finally, the web formation detection means may take the form of an array of linescan cameras arranged across the moving web.

In another further preferred embodiment, the paper web formation analyzer can be used both on paper machines operating at high speed and on cut samples as a desk top unit to unify formation evaluation for both situations.

The preferred analyzer, according to this invention, offers the following advantages: the ability to analyze paper web formation; the ability to be used both online/offline; the ability to unify formation evaluations; good stability; good durability; and excellent economy. In fact, in many of the preferred embodiments, these factors of paper web formation analysis, use for both online/offline, unification of formation evaluations, and excellent economy are optimized to an extent that is considerably higher than heretofore achieved in prior, known paper web formation analyzers.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

Sheet formation is a measure of the relative uniformity of a light transmitted through the sheet. Localized variations of light transmission can be due to fiber flocs and voids. The smaller and more uniform these variations, the better the formation. In the limiting case, the "perfect" sheet would transmit exactly the same amount of light uniformly throughout its total area, thereby giving a milky appearance.

One can envision quantifying localized light variations from an 8.5" by 11" sample on a 0.030" by a 0.030" grid of gray-scale values where 0 is pure black and 255 is pure white, with values in between. The average of the grid points might be 200, for example, but the values at grid points can range from 185 to 215.

Imagine building a histogram with intensity values on the x-axis and number of grid point occurrences on the y-axis. A conventional off-line formation tester as discussed earlier determines a "formation index" based on the histogram peak height divided by the histogram band width.

Figure 1:
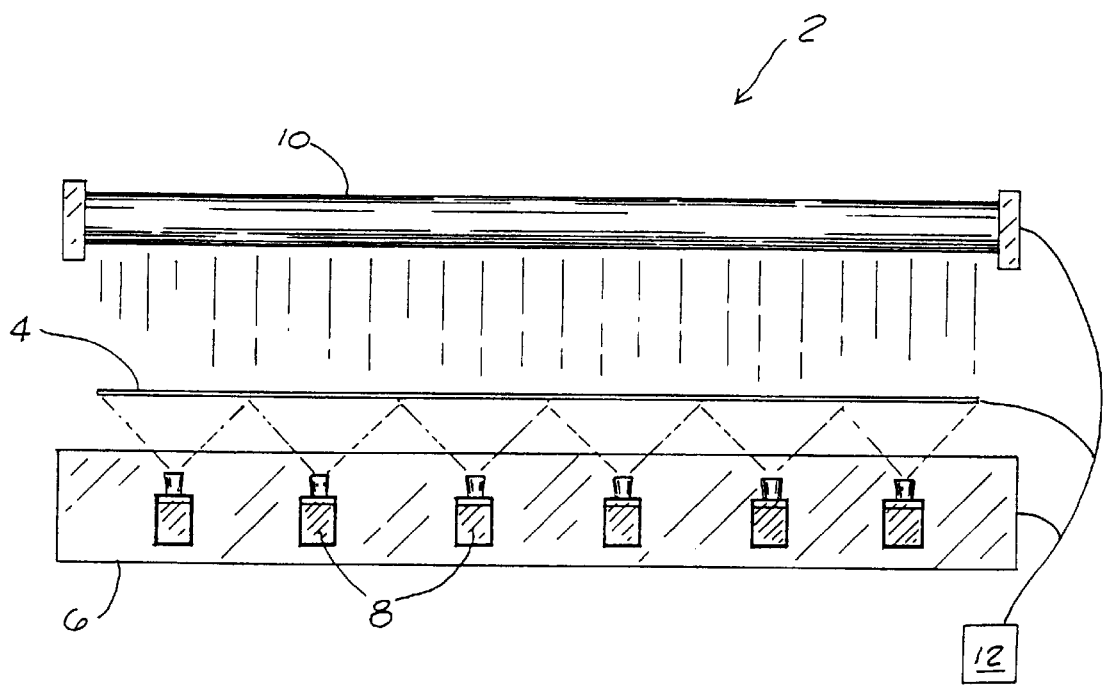
FIG. 1 is a schematic illustration of a unified online/offline paper web formation analyzer, according to the present invention.

With reference to FIG. 1, there is illustrated a unified online/offline paper web formation analyzer 2. Analyzer 2 includes, in part, paper web/sheet 4, light array cabinet 6, a plurality of lights 8, light sensor 10 and conventional tachometer 12.

Preferably, cabinet 6, lights 8 and sensor 10 employ a fiber optic light source and linescan camera, such as, that manufactured by Isys of Midlothian, Va., under the Isys Controls Vision System. However, for the present invention, the fiber optic light source and linescan camera will be placed in a transmitted light configuration.

During the operation of the analyzer 2, the linescan camera or sensor 10 records a linear array of 2,048 gray scale values, which would be spread across the cross-direction (CD) of paper sample 4. Input from tachometer 12, which will be discussed later, from a set of given controllers (for the offline device) serves to trigger the camera 10 to record line after line of data. Each line of data is transmitted to a conventional computer (not shown), where a two-dimensional array is formed. After recording (enough) data on the down web (MD) direction, the formation analysis would begin.

To develop this even further, the method for determining paper web formation would be as follows:

1.) Feed a sample 4 into the analyzer 2.
2.) The computer specifies the light source intensity of light cabinet 6 to an "average" value.
3.) Perform a scan analysis of sheet 4 with the specified light source intensity by moving sheet 4 through the linescan area.
4.) Compute the average gray scale value of received light.
5.) Was the gray-scale value within the specified target average (for example, 180–190)?
6.) If no, increase (or decrease) light source intensity and repeat step 2 by backing up sample 4 through analyzer.
7.) If yes, record the gray scale matrix of received intensities.
8.) Perform the computations in the computer and report the result.

Figure 2:
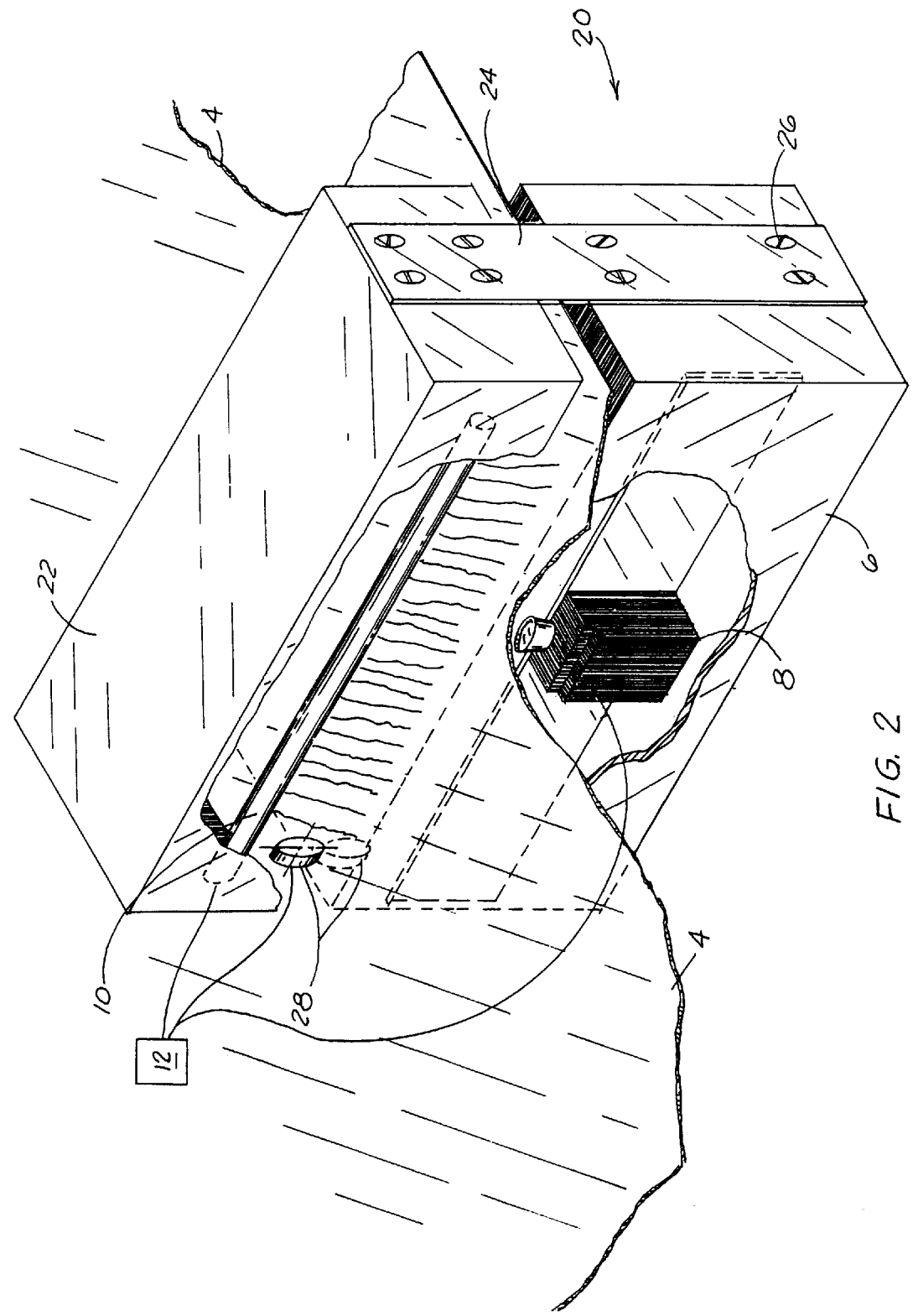
FIG. 2 is an isometric view of the paper web formation analyzer being employed online on a paper machine, according to the present invention; and, FIG. 3 is an isometric view of the paper web formation analyzer being used offline as a desk top unit, according to the present invention.

With reference to FIG. 2, there is illustrated an on-line version 20 of analyzer 2. In particular, on-line analyzer 20 includes, in part, paper web 4, light cabinet 6, light source 8, camera 10, tachmometer 12, camera cabinet 22, conventional bracket 24, conventional fasteners 26, and pinch rollers 28.

During the operation of analyzer 20, an array of cameras 10 (only one camera being shown for convenience) is arranged across the moving web 4 and intercepts the light reflected off of web 4 in a single thin 0.010" line in the cross-direction (CD). Tachometer 12 mounted on pinch rollers 28 having a nip provides a synchronized pulse to make camera 10 intercept line after line of intensity data to form up a continuous two-dimensional reflected light gray-scale image. In this manner, the machine tachometer 12 drives the camera speed to obtain a two-dimensional gray-scale image over a specified down web (MD) distance.

The formation mathematics are worked out in the computer (not shown) and displayed for that distance. That image will be flushed from computer memory, then the data gathering and computation processes will be repeated, providing a psuedo-continuous measure of sheet formation.

Figure 3:
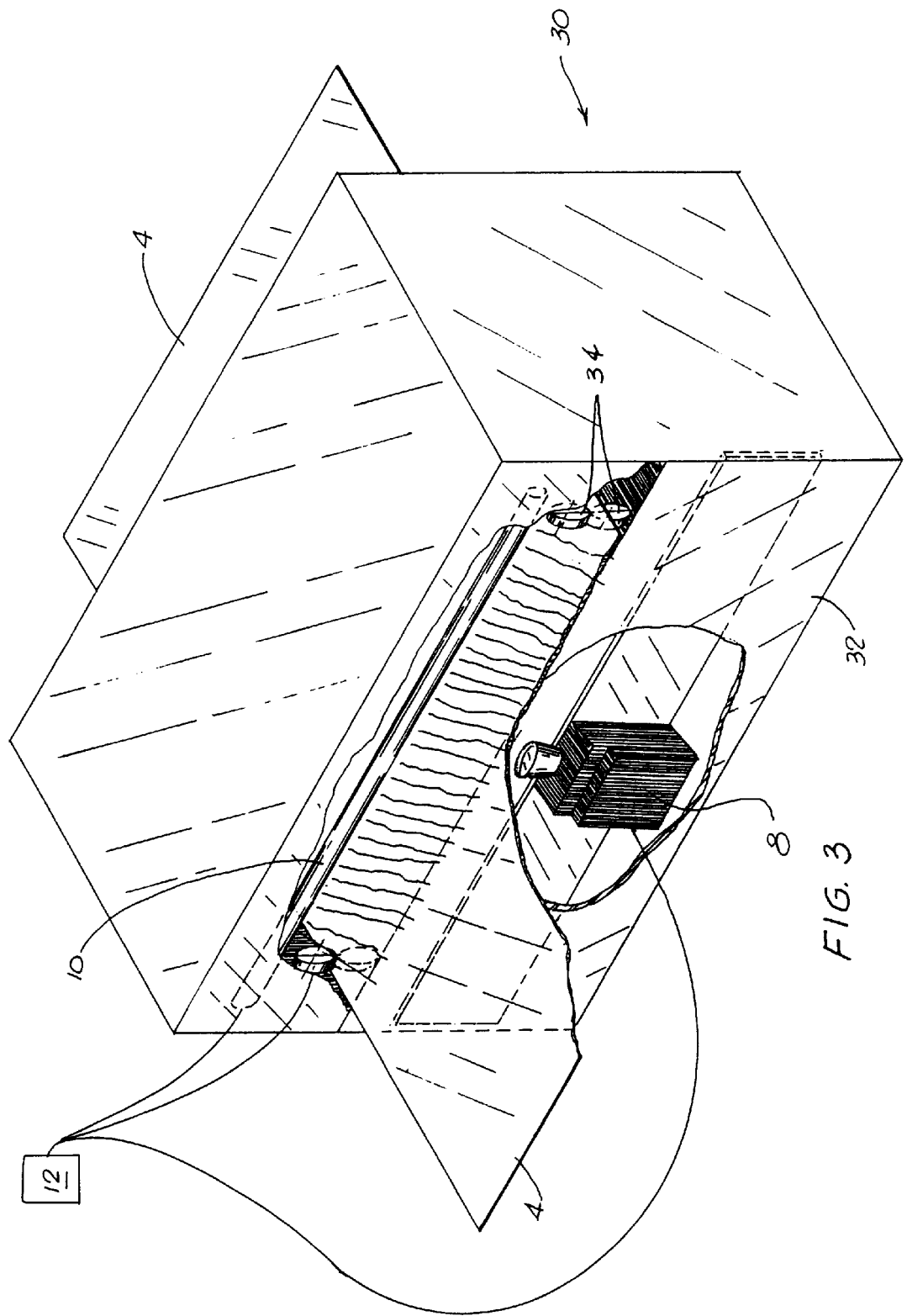

Finally, FIG. 3 illustrates an off-line version 30 of analyzer 2. In particular, off-line analyzer 30 includes, in part, paper sheet 4, light source 8, camera 10, tachometer 12, cabinet 32, and pinch rollers 34 having a nip.

During the operation of off-line analyzer 30, a single sample 4 to be tested would be fed into analyzer 30. Pinch rollers 34 would grab sample 4 at the nip and feed sample 4 through the test position at a constant speed, fixing camera sample speed as discussed earlier. Once the entire image is recorded, the formation mathematics would be determined by a computer and the results would be displayed as discussed earlier.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. An on-line/off-line paper web formation analyzer, wherein said analyzer is comprised of:

a paper web having first and second sides;

a paper web translating means, wherein said paper web translating means is further comprised of at least one pair of rollers having a nip located substantially between said rollers, wherein said rollers are further comprised of a plurality of pinch rollers which substantially contact said paper web at said nip;

a plurality of stationary paper web illumination means located substantially adjacent to said first side of said paper web, wherein said illumination means are further comprised of fiber optic lights;

a plurality of stationary paper web formation detection means located substantially adjacent to said second side of said paper web and substantially above said illumination means, wherein said formation detection means are further comprised of a plurality of linescan cameras; and a paper web translating rate measurement and illumination/detection synchronization means operatively connected to said paper web translating means, said illumination means and said detection means wherein said paper web translating rate measurement and illumination/detection synchronization means is further comprised of a tachometer.

* * * * *